United States Patent [19]

Conn et al.

[11] 4,424,054

[45] Jan. 3, 1984

[54] FLUID-EXPANSIBLE CONTRACEPTIVE TAMPON AND APPLICATOR

[75] Inventors: Shepard Conn, Metuchen, N.J.; Arnold Kushner, Queens, N.Y.

[73] Assignee: KCDP Corporation, New York, N.Y.

[21] Appl. No.: 268,381

[22] Filed: May 29, 1981

Related U.S. Application Data

[63] Continuation-in-part of Ser. No. 906,984, May 17, 1978.

[51] Int. Cl.[3] .............................................. A61F 15/00
[52] U.S. Cl. ........................................ 604/11; 604/12
[58] Field of Search .................. 128/263, 270, 285; 604/2-3, 11-12, 14-18, 73, 104, 285, 200

[56] References Cited

U.S. PATENT DOCUMENTS

| | | | |
|---|---|---|---|
| 3,335,726 | 8/1967 | Maranto | 128/270 |
| 3,512,528 | 5/1970 | Whitehead et al. | 128/285 |
| 3,698,812 | 10/1972 | Jaycox | 128/263 |
| 4,186,742 | 2/1980 | Donald | 128/270 |
| 4,228,797 | 10/1980 | Dickey | 128/270 |
| 4,318,405 | 3/1982 | Sneider | 128/263 |

OTHER PUBLICATIONS

Page, Ernest W., M. D., "Experiences with a Tampon–Spermicide Device" *Contraception*, vol. 23, No. 1, (Jan. 1981), pp. 37–44.

Singh, B. and Cutler, J. C., "Vaginal Contraceptives for Prophylaxis Against Sexually Transmissible Diseases" In: Zatuchni, G. I. et al. (editors), *Vaginal Contraception: New Developments* (Hagerstown, MD Harper & Row), pp. 175–185.

*Primary Examiner*—C. Fred Rosenbaum
*Assistant Examiner*—Sherri E. Vinyard
*Attorney, Agent, or Firm*—Lane, Aitken & Kananen

[57] ABSTRACT

An apparatus for moistening a tampon with a spermicidal, bactericidal and/or virucidal fluid and expelling the tampon includes an open ended tampon storing member for storing the tampon in an unactivated state and a reservoir member for storing the fluid. The reservoir member has a closed inner end slidably received in the tampon storing member and a closed outer end extending out of the tampon storing member. In several embodiments, the reservoir member includes an elongated element to effect fluid flow through a dispensing opening in the inner end and through a vent opening in the outer end. In another embodiment, the inner end of the reservoir member is closed by a wall which is fragible under radially applied pressure to form a dispensing opening and the other end is closed by a wall having an element which is frangible to form a vent opening.

19 Claims, 6 Drawing Figures

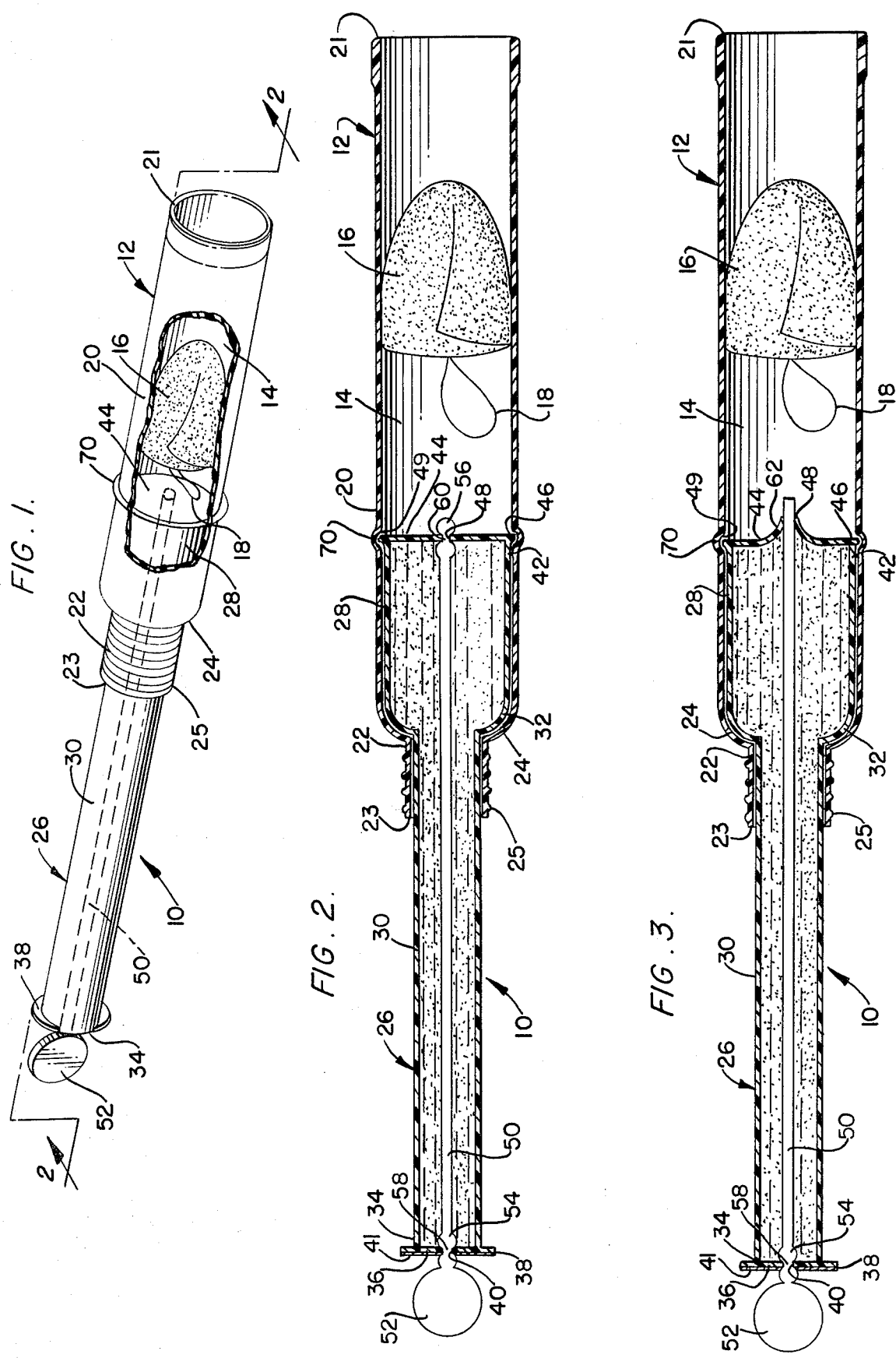

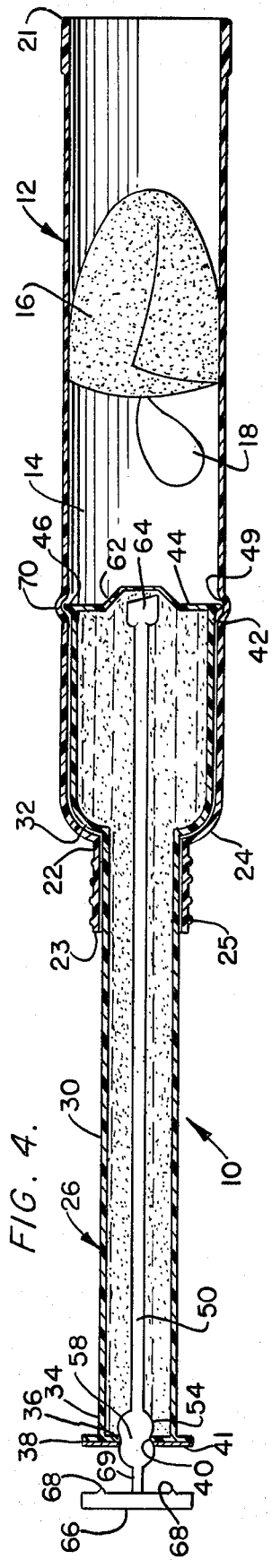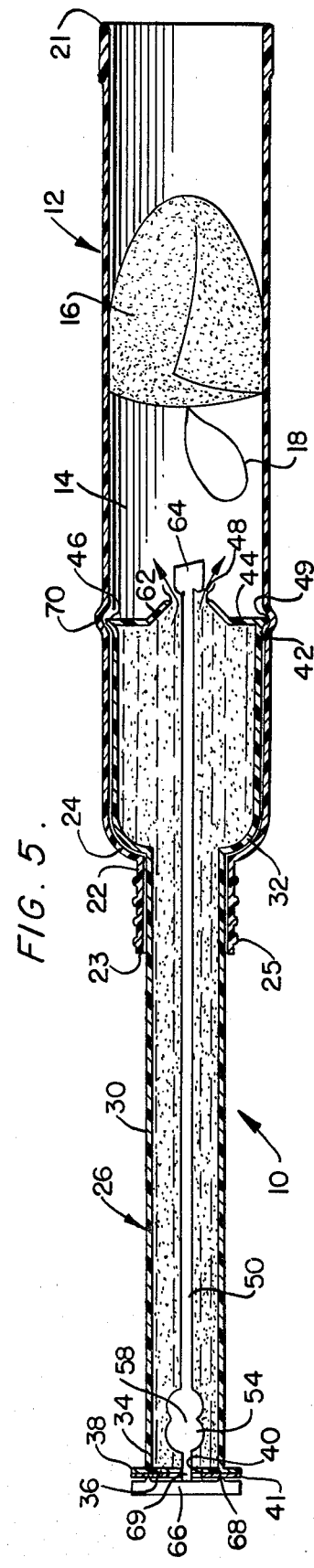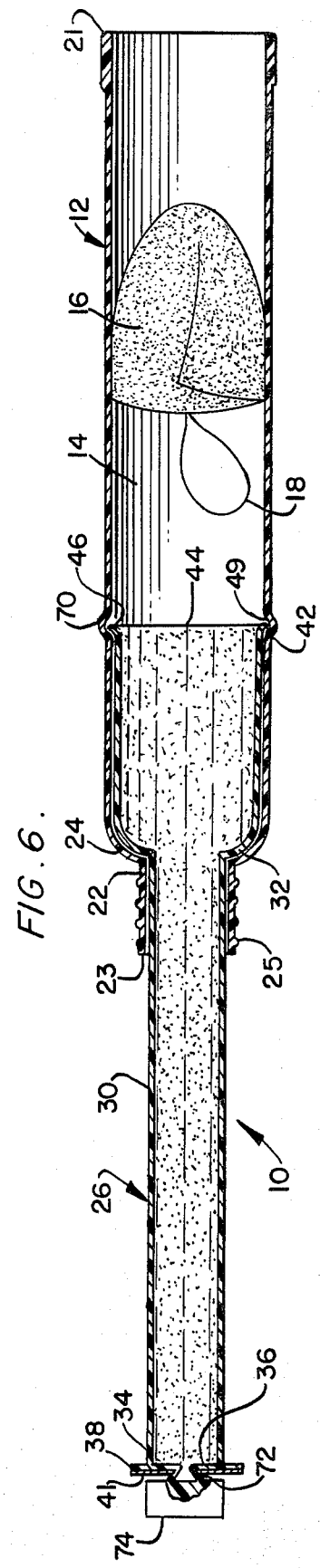

FLUID-EXPANSIBLE CONTRACEPTIVE TAMPON AND APPLICATOR

CROSS REFERENCE TO RELATED APPLICATION

This application is a continuation-in-part of Ser. No. 906,984, filed May 17, 1978.

BACKGROUND OF THE INVENTION

This invention relates to an apparatus for moistening and dispensing a tampon. More particularly, this invention relates to an applicator which houses a tampon made from, preferably, a hydrophilic, fluid-expansible material in a quiescent, compressed, unactivated state in a first chamber separate from a second chamber, which acts as a reservoir for a spermicide, bactericide, virucide or other substance, usually in fluid form. The applicator includes means for bringing the fluid into contact with the tampon upon command prior to use, as well as means for delivering the moistened tampon to a vagina and positioning it therein. Still more particularly, this invention relates to a combination of an applicator of the type described with a tampon made from a body of purposefully-compressed, memory-retentive, hydrophilic, fluid-expansible material with a high coefficient of expansion, which is resilient when moistened or activated prior to insertion into a vagina.

Mankind has long sought an effective method and apparatus for contraception for purposes of population control, for family planning, and for preventing unwanted pregnancies. While a number of contraceptive techniques have been proposed, many of which have been clinically effective, each has suffered from various types of shortcomings for a number of reasons. For example, the use or oral contraceptives has been found to be associated with a number of adverse side effects, some of which are fatal. Also, intrauterine devices have been known to cause lesions, and even to perforate the uterus. Furthermore, IUD's are spontaneously rejected from the uterus in a siginificant number of women.

The so-called barrier type of contraceptive has long been included among such contraceptive proposals. Many barrier contraceptives are efficient and benign. However, they often require special motivation for their use by reason of the fact that they may initially, especially if rigid or semi-rigid, have to be fitted precisely by a physician. Even more importantly, in actual use, they are unesthetic and therefore unacceptable to many women. Furthermore, many barrier contraceptives require application just prior to coitus and may be said to be coitally-related, a factor which discourages their use.

By way of background, the human vagina may be considered to be a closed-end collapsed cylinder. The uterine cervix, which varies from 1 to 4 cm in length, protrudes into the closed end. The uterine cervix may point directly into the axis of the cylinder, or backward (which is the most common orientation) or forward. The spaces around the cervix are called fornices and include an anterior, a left, a right, and a posterior fornix. A contraceptive barrier, to be effective, must be in contact with the cervix to block the os uteri, and ideally should fill all of the fornices to prevent the inadvertent migration of semen into the cervical mucus.

An intravaginal anticonception tampon was referred to in the Papyros Ebers, circa 1550 B.C., and has been in use in one form or another for more than 3500 years. However, there have been no reliable scientific reports of its efficacy. Such tampons have included sponges moistened with fluid having spermicidal qualities. At least as early as the time of the ancient Egyptians, a tampon of lint impregnated with drugs and honey was said to be capable of contraceptive qualities when placed in the vagina of the user. Later, but at least as early as the nineteenth century, a suitable soft sponge tied by a ribbon and properly placed high in the vagina, was said to possess contraceptive qualities. Thus, historically, it is known that a suitable sponge properly placed in contact with all vaginal fornices and well moistened with an effective spermicidal solution should act as an effective contraceptive by virtue of (1) its barrier action, (2) its absorption and retention of ejaculate, and (3) its prolonged spermicidal action.

It has remained a problem of convenience and esthetics for the user of a resilient barrier-type contraceptive to prepare and insert it into a vagina prior to intercourse. In addition to the actual or perceived non-esthetic qualities of such a preparatory act, such preparations may be inconvenient, susceptible to miscalculation such as by insufficient or excess moistening with spermicide, the premature or tardy application of spermicide, and the like. Accordingly, it is an overall object of this invention to provide a suitable contraceptive tampon of barrier design and function made from absorbent material which can be impregnated with a precisely metered amount of spermicide in an applicator and conveniently inserted into the vagina by using the applicator in such a way that the moistened tampon material acts as an effective contraceptive. The applicator, after having served to moisten the tampon and to insert it into the vagina, is disposed of. The tampon is intended to remain in place, once positioned in the vagina, for as long as 24 hours, during which time coitus may take place one or more times. Thereafter, it is removed and disposed of by the user.

While the prior art has focused its attention on compressible sponge-like members, such as those made from sea sponges, or viscose and cellulose materials whose shape in the quiescent state is approximately the same as its shape in the active implanted state, it is another purpose of this invention to utilize a compressed (without having to be physically restricted to enforce compression), dry tampon material which can be moistened with an effective spermicidal solution immediately prior to vaginal insertion. When moistened, the compressed material expands markedly either prior to or after introduction into the vagina. By using such an expansible material, the contraceptive tampon, in the dry, unactivated state, can be stored in a small, handy compartment in an applicator, and can expand to a clinically effective size after moistening to serve as a barrier to the os uteri and, at the same time, also fill the fornices.

In order to improve the convenience and the esthetic character of the contraceptive act, it is a significant aspect of this invention to provide an applicator for the expansible hydrophilic tampon in which the tampon is retained in a chamber separate from a reservoir for spermicidal solution. It is the aim of this invention to bring the spermicide, upon command, into contact with the tampon to expand it to its active size and shape, and to use the applicator as an insertion device for inserting the tampon into its intended position.

It is another object of this invention to provide a disposable, compact applicator-tampon system which can be conveniently used to wet the tampon with a spermicide stored in the applicator and to insert it into the vagina with a minimum of manipulations and moving parts.

It is a further object of this invention to provide a new use as a barrier contraceptive for a purposefully-compressed, memory-retentive, hydrophilic material which in its unactivated state is compact, but which becomes resilient and absorbent as it expands to a clinically effective size and shape upon moistening with a spermicide or medicament.

In addition, to the need for contraception, there exists the need for treating and preventing the spread of sexually transmissible diseases. It is known that some spermicides act as medicaments as well, and that such bactericides as chloramine, benzethonium chloride and chinosol are used in current contraceptive technology. Furthermore, some spermicides are anti-viral agents. Therefore, it is another object of the present invention to use a bactericide, virucide or a combined agent for disease prophylaxis and contraception in an applicator for dispensing a moistened tampon.

A problem associated with the use of tampons which has been widely publicized is the occasional adverse effect on the health of tampon users, known as toxic shock syndrome. The problem is caused by toxins produced by an organism known as Staphlococcus aureus. Consequently, it is yet another object of the present invention to provide an apparatus containing a bactericide, for dispensing a tampon moistened with the bactericide for combatting Staphlococcus aureus.

These and other objects of the invention will become apparent from the following description of preferred embodiments of the present invention taken in conjunction with the accompanying drawings.

BRIEF SUMMARY OF THE INVENTION

Directed to achieving the aforestated objects and overcoming the problems associated with prior art barrier-type contraceptive devices and prior art tampons, the invention, in one aspect, relates to a compact, disposable applicator which comprises at least a pair of telescoping, generally cylindrical members made from a pliant plastic material. One of the cylindrical members acts as a reservoir for a precisely metered amount of spermicide, bactericide, virucide or other fluid medicament and is thus closed. The reservoir member includes a closed end adjacent to a tampon stored in its dry unactivated state in a chamber defined by the other cylincrical tampon storing member. The end of the reservoir member opposite the closed end defines a vent and filler opening to permit the reservoir member to be filled and the vent to be sealed. Preferably, the closed end of the reservoir member is openable by the user to release at least a small amount of spermicide, bactericide, virucide or other fluid medicament from the resrvoir member to the fluid-expansible tampon.

Upon contact with the small amount of released fluid, the adjacent portion of the fluid-expansible tampon expands within the tampon storing member. Thereafter, the remaining fluid is released to wet and expand the entire tampon to the desired degree. After the tampon is moistened within the tampon storing member by the fluid, the reservoir member is caused to telescope within the tampon storing member while the tampon storing member is positioned within the vagina to insert the tampon into position in the vagina. Release from the applicator permits the tampon to expand further and, where the tampon is a contraceptive tampon, to act as a clinically effective barrier to the os uteri, to fill the fornices, and to further act as an absorbent for ejaculate, particularly in cases of repeated intercourse.

It is a second feature of this invention to provide a new use as a barrier contraceptive for a compressed, memory-retentive, hydrophilic, fluid-expansible material which can be stored in an unactivated state in a compact manner and yet can become resilient and expand into a desired size and shape for insertion and upon insertion into the vagina of the user. Such materials are well known in other arts and have a high degree of expansibility when wetted. For purposes of this specification, the "quiescent state" of the tampon refers to its unactivated, compressed state prior to impregnation with a fluid and prior to insertion into the body of the user. Similarly, the "dry" state of the compressed hydrophilic material, for example, one made of cellulose, refers to the state of the material prior to impregnation with a spermicide, bactericide, virucide or other medicament, while including a normal moisture level inherent in such material or in the normal environment for the material within the applicator. Such materials are memory-retentive. That is, the materials can be purposefully heated to expel moisture and compressed to a desired compact size, thereby compressing and collapsing the cellular structure of the material. Such materials thus retain the collapsed or compressed state in the absence of the application of moisture without requiring physical restrictions or retraints. Such materials are commercially available. Example of suitable materials are those known in the trade as "Supercel" and "Normandy", available from the American Sponge & Chamois Co. of Long Island City, New York.

In the applicator according to the present invention, the cylindrical member of the applicator acting as the reservoir includes a closed end operable to release the fluid and an opposite end defining a vent and filler opening. In several of the preferred embodiments, an elongated element in the reservoir member is movable with respect to the ends of the reservoir member to produce a dispensing opening in one end and a vent opening in the opposite end. A portion of the elongated element extends outside the reservoir member and defines a gripping surface so that the elongated element can be moved by hand with respect to the reservoir member. In two of the preferred embodiments, the elongated element defines valve elements forming seals with the ends of the reservoir member, the elongated element being movable with respect to the ends to define openings. In another preferred embodiment, the elongated element defines a valve element at one end and a puncturing element for rupturing an opening in the other end. In still another embodiment of the invention, the elongated element is eliminated and the closed end of the reservoir member is provided with score lines or other weaknesses, so that it is readily frangible upon the application of radially directed pressure. The opposite end of the reservoir member defines a frangible element provided with a gripping tab, so that the user can make a vent opening in the reservoir member.

These and other features of the invention are described hereinafter in the detailed description of the invention taken in conjunction with the drawings.

BRIEF DESCRIPTION OF THE DRAWINGS

FIG. 1 is a perspective view of a tampon applicator according to a preferred embodiment of the present invention;

FIG. 2 is a cross section along the line 2—2 of the tampon applicator of FIG. 1;

FIG. 3 is a cross section of another preferred embodiment of the applicator;

FIG. 4 is a cross section of still another embodiment of the applicator prior to the release of liquid;

FIG. 5 is a cross section of the applicator of FIG. 4 after the release of the liquid; and FIG. 6 is a cross section of yet another embodiment of the applicator.

DETAILED DESCRIPTION OF THE PREFERRED EMBODIMENT

As shown in FIGS. 1 and 2, the applicator according to the present invention is designated generally by the reference numeral 10. The applicator 10 includes a first generally cylindrical tampon storing member 12 defining an open-ended chamber 14 for storing a folded compressed tampon 16 which, upon wetting, can act as a contraceptive, bactericidal and/or virucidal tampon, as will be discussed in greater detail later in the specification. The tampon 16 has a string or cord 18 secured thereto to allow easy removal of the tampon 16 from the vagina when disposal is appropriate. If desired, the chamber 14 may be closed by a removable cover member secured to the member 12.

The tampon storing member 12, which is preferably made from a flexible thin-wall plastic material, has a body portion 20 which defines an outer end 21, and a neck portion 22 which defines an inner end 23. The body portion 20 and the neck portion 22 are connected by a shoulder 24, and the neck portion 22 defines a series of ridges 25 or some other structure to insure that the neck portion 22 can be firmly gripped by the user. The outer end 21 of the body portion 20 is preferably rounded, and the exterior wall of the tampon storing member 12 is preferably smooth to avoid irritation of the tissues of the vagina when the tampon storing member 12 is inserted to expel the tampon 16.

The tampon storing member 12 is adapted to receive a reservoir member 26 in a telescoping relationship. The reservoir member 26 includes a piston portion 28 comfortably slidable within the body portion 20, a shaft portion 30 slidable within the neck portion 22 and a shoulder 32, which connects the piston portion 28 and the shaft portion 30 and engages an internal surface of the shoulder 24 of the tampon storing member 12 to limit the travel of the reservoir member 26 with respect to the tampon storing member 12.

The reservoir member 26 has an outer end 34 closed by a wall 36 secured to the outer end 34, the wall 36 extending radially beyond the shaft portion 30 to define flanges 38. The wall 36 also defines a central opening 40 which serves as a filler and vent opening. A label 41 having pertinent information, such as the contents of the applicator 10 and the amount of fluid in the reservoir member 26, can be affixed to the outer surface of the wall 36. The reservoir member 26 also has an inner end 42 closed by a wall 44 secured to the inner end 42 whereby the reservoir member 26 defines a reservoir, the wall 44 forming a flange 46 extending radially beyond the piston portion 28. The wall 44 defines a central opening 48 for dispensing its contents into the tampon storing member 12 for moistening the tampon 16.

The reservoir member 26 is filled with a spermicidal fluid, a bactericidal fluid or a virucidal fluid, or with a fluid which acts as a combination of these fluids. Among the fluids contemplated for use with the present invention are such bactericides as chloramine, benzethonium chloride and chinosol, which are currently used in contraceptive technology. In addition, some fluids which are commonly thought of as spermicides are also anti-viral agents. They and other virucides also are contemplated for use in the present invention.

The flanges 38 abut the inner end 23 of the tampon storing member 12 when the reservoir member 26 is completely telescoped into the interior of the tampon storing member 12. The flanges 38 define a convenient surface engageable by the hand of the user to move the reservoir member 26 into the tampon storing member 12. The flange 46 on the wall 44 secured to the inner end 42 of the reservoir member 26 has a diameter slightly greater than the inner diameter of the body portion 20 of the tampon storing member 12. To accommodate the flange 46, an annular groove 49 is formed in the interior surface of the body portion 20 and is spaced from the shoulder 24 a distance approximately equal to the distance between the flange 46 and the shoulder 32 on the reservoir member 26, so that the annular groove 49 receives the flange 46 when the reservoir member 26 is fully retracted with respect to the tampon storing member 12. The flange 46 is flexible, so that the reservoir member 26 is releasably held in the retracted position and may be moved by a force sufficient to flex the flange 46.

An elongated element 50 extends axially through the reservoir member 26 from the outer end 34 to the inner end 42 and includes a gripping portion extending beyond the outer end 34 to permit manipulation of the elongated element 50 by the hand of the user so that fluid in the reservoir member 26 can be released. In the embodiment shown in FIG. 1, the elongated element 50 is in the form of a plunger made of a relatively rigid material, such as a rigid plastic, having a pull tab 52 comprising a gripping portion on the extending portion. The elongated element 50 has a pair of sealing elements in the form of bulbous formations 54 and 56, one positioned at each end of the reservoir member 26, each bulbous formation 54, 56 having an annular groove 58 and 60, respectively. The bulbous formations 54 and 56 are positioned in the vent opening 40 and the dispensing opening 48, respectively, defined in the walls 36 and 44 at opposite ends of the reservoir member 26. The material of the walls 36 and 44 defining the openings 40 and 48 forms seals with the bulbous formations 54 and 56 in the annular grooves 58 and 60. When the elongated element 50 is partially withdrawn from the reservoir member 26 by pulling on the pull tab 52, the bulbous formations 54 and 56 move out of the vent opening 40 and the dispensing opening 48, thereby effecting the flow of the fluid contents of the reservoir member 26 out of the dispensing opening 48 into the tampon storing member 12, where they are absorbed by the tampon 16, and the flow of air through the vent opening 40 in the reservoir member 26.

In assembly and manufactures, before the wall 44 is secured to the inner end 42 of the reservoir member 26, the elongated element 50 is inserted in the reservoir member 26 until the bulbous formation 54 fills the vent opening 40 to form a fluid-tight seal. Then the reservoir member 26 is inverted and a metered amount of fluid is poured into it. The wall 44 is forced onto the bulbous formation 56 of the elongated element 50, thereby sealing the dispensing opening 48. The wall 44 is, thus, in position so that it engages the inner end 42 of the reservoir member 26 to which it is secured as by welding or cementing.

Another embodiment of the applicator 10, as is illustrated in FIG. 3, is similar to the embodiment shown in FIGS. 1 and 2, but differs in that the wall 44 which closes the inner end 42 of the reservoir member 26 has a frustoconical depression 62 which initially has a bottom defined by a thin, conformable membrane. There is no bulbous formation at the end of the elongated element 50 adjacent the inner end 42 of the reservoir member 26. Instead, the straight rod shape of the elongated element 50 ruptures the conformable membrane during assembly and forms a fluid-tight seal therewith.

In operation, the elongated element 50 is grasped by the pull tab 52 and withdrawn from the reservoir member 26. The elongated element 50 moves away from the dispensing opening 48 it created by rupturing the membrane, thereby allowing a small amount of the contents of the reservoir member 26 to moisten and expand the tampon 16, thus forming a tight seal in the tampon storing member 12. Simultaneously, the bulbous portion 54 moves out of the vent opening 40 in the outer end 34, thereby venting the reservoir member 26 to allow the remainder of the contents to flow out of the dispensing opening 48 into the tampon 16.

As is illustrated in FIGS. 4 and 5, still another embodiment of applicator 10 according to the present invention includes the bulbous formation 54 for sealing the vent opening 40 at one end of the reservoir member 26, and the wall 44 sealing the inner end 42 of the reservoir member 26 including the frustoconical depression 62 having the rupturable membrane at its bottom. The elongated element 50 includes a puncturing member 64 having a sharp edge, the puncturing member 64 being wider than the rest of the elongated element. The extending portion of the elongated element 50 has a gripping element defined by a push bar 66 rather than a pull tab, so that the elongated element 50 can be pushed farther into the reservoir member 26. As can be seen in FIG. 4, this movement results in the puncturing member 64 puncturing the dispensing opening 48 in the membrane at the bottom of the frustoconical depression 62. The vent opening 40 is enlarged to accommodate the insertion of the puncturing member 64, and the bulbous formation is enlarged to correspond to the enlarged vent opening 40.

A plurality of nibs 68 are defined on the underside of the push bar 66 to maintain the push bar 66 spaced a slight distance from the wall 36 closing the outer end of the reservoir member 26 to cooperate with a thinned neck 69 in the elongated element 50 between the push bar 66 and the bulbous formation 54 in insuring an air passage for venting. The distance between the nibs 68 and the wall 36 when the bulbous formation 54 is in its sealing position is chosen so that, when the push bar 66 is pushed to the point where the nibs 68 engage the wall 36, the puncturing member 64 will pass completely through the rupturable membrane, thereby providing a space between the puncturing member 64 and the dispensing opening 48 so that fluid may flow out past the puncturing member 64. At the same time, the bulbous formation 54 is forced out of the vent opening 40 and into the reservoir member 26 to enable a smooth flow of the spermicide, bactericide, virucide or other substance through the dispensing opening 48.

In manufacturing and assembling the embodiment illustrated in FIGS. 4 and 5, the reservoir member 26 can be filled by two alternate methods. According to the first method, with the wall 44 secured to the inner end 42 but without the elongated element 50 in place, the fluid is directed through the vent opening 40 until the reservoir member 26 is filled to a specified level. Then the elongated element 50 is inserted through the vent opening 40 until the groove 58 in the bulbous formation 54 is seated in the vent opening 40 to form a seal with the wall 36. According to the second method, the elongated element 50 is in place, with the bulbous formation 54 sealing the vent opening 40, but with the inner end 42 open. The reservoir member 26 is then inverted and filled to a specified level, whereupon the wall 44 is heat sealed to otherwise suitably attached to the inner end 42.

Another embodiment according to the present invention, as illustrated in FIG. 6, operated without the use of an elongated element. Instead, the wall 44 of the inner end 42 of the reservoir member 26 is a frangible member having score lines or other form of weakening, so that the wall 44 can be ruptured by pressure applied radially through the tampon storing member 12. As mentioned earlier, the tampon storing member 12 is made of a flexible plastic material, which is deformable under radial force, so that radial force can be applied to break the frangible member and form a dispensing opening. The annular groove 49 is defined within an annular ridge 70 which protrudes from the tampon storing member 12 and serves to indicate the location at which radial pressure should be applied. Such score lines are described in more detail in the previously mentioned copending application, Ser. No. 906,984, now U.S. Pat. No. 4,271,835.

A frangible element 72, such as a frangible neck is defined on the wall 36 at the outer end 34 of the reservoir member 26. A tear tab 74 is connected to the frangible element 72 so that it can be conveniently grasped and sufficient tearing force can be applied to the frangible element 72 to cause its failure and to effect a vent opening in the wall 36.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. An apparatus for intravaginally expelling an activated tampon comprising:
   a tampon storing member defining a chamber for receiving and storing therein said tampon in a quiescent unactivated state, said tampon being activated by a fluid;
   a reservoir member storing said fluid therein separate from and out of contact with said tampon;
   manually-activatable means for releasing said fluid from the reservoir member to activate the tampon with said fluid while the tampon is retained in said tampon storing member prior to intravaginal insertion; and means, including the structural cooperation of said tampon storing member and said reservoir member, for intravaginally expelling said tampon in its activated state from said apparatus into a vagina, wherein said fluid releasing means includes means for effecting fluid flow through a dispensing opening and a separate venting opening in said reservoir member.

2. The apparatus of claim 1 wherein the means for effecting fluid flow includes an elongated element.

3. The apparatus of claim 2 wherein the reservoir member has an outer end wall and an inner end wall, and the elongated element extends from the outer end wall to the inner end wall.

4. The apparatus of claim 3 wherein the elongated element is movable with respect to the outer end wall and the inner end wall of the reservoir member to effect fluid flow through a dispensing opening in one of said end walls and a vent opening in the other of said end walls.

5. The apparatus of claim 1 wherein the fluid is a spermicide.

6. The apparatus of claim 1 wherein the fluid is a bactericide.

7. The apparatus of claim 1 wherein the fluid is a spermicide and a bactericide.

8. The apparatus of claim 4 wherein the elongated element includes a portion extending beyond one end wall of the reservoir member, said portion being grippable by a user.

9. The apparatus of claim 4 wherein the elongated element includes a sealing element forming a seal with one end wall of the reservoir member.

10. The apparatus of claim 4 wherein the elongated element includes two sealing elements, one sealing element forming a seal with one end wall of the reservoir member and the other sealing element forming a seal with the other end wall of the reservoir member.

11. The apparatus of claim 4 wherein the elongated element includes means for rupturing one end wall of the reservoir member.

12. The apparatus of claim 11 wherein the rupturing means includes a sharp edge.

13. The apparatus of claim 1 wherein the reservoir member is slidingly received in the tampon storing member so that the sliding movement of the reservoir member in the tampon storing member expels the tampon.

14. The apparatus of claim 12 wherein the inner wall of the reservoir member includes a flexible flange extending radially from the reservoir member into an annular groove in the tampon storing member, whereby the reservoir member is releasably held in the retracted position.

15. An apparatus for intravaginally expelling an activated tampon from said apparatus comprising:

a tampon storing member defining a chamber receiving and storing therein said tampon in a quiescent unactivated state, said tampon being activated by a fluid;

a reservoir member defining a reservoir storing said fluid therein separate from and out of contact with said tampon;

manually-activatable means for releasing said fluid from the reservoir member to activate the tampon with said fluid while the tampon is retained in said tampon storing member prior to intravaginal insertion; and means, including the structural cooperation of said tampon storing member and said reservoir member for intravaginally expelling said tampon in its activated state from said apparatus into a vagina, wherein said fluid releasing means includes a frangible wall in said reservoir member for defining a dispensing opening and a separate frangible element for defining a vent opening.

16. The apparatus of claim 15 wherein a grasping tab is provided on the separate frangible element.

17. The apparatus of claim 15 wherein the fluid is a spermicide.

18. The apparatus of claim 15 wherein the fluid is a bactericide.

19. The apparatus of claim 15 wherein the fluid is a spermicide and a bactericide.

* * * * *